(12) United States Patent
Haas

(10) Patent No.: US 10,299,893 B2
(45) Date of Patent: May 28, 2019

(54) METHOD AND APPARATUS FOR SLOW PALATE EXPANSION

(71) Applicant: Andrew Haas, Silver Lake, OH (US)

(72) Inventor: Andrew Haas, Silver Lake, OH (US)

(*) Notice: Subject to any disclaimer, the term of this patent is extended or adjusted under 35 U.S.C. 154(b) by 0 days.

(21) Appl. No.: 15/596,778

(22) Filed: May 16, 2017

(65) Prior Publication Data

US 2018/0333227 A1    Nov. 22, 2018

(51) Int. Cl.
*A61C 7/10* (2006.01)
*A61C 7/28* (2006.01)
*A61C 7/12* (2006.01)

(52) U.S. Cl.
CPC .............. *A61C 7/10* (2013.01); *A61C 7/282* (2013.01); *A61C 7/12* (2013.01)

(58) Field of Classification Search
CPC .. A61C 7/10; A61C 7/20; A61C 7/125; A61C 7/282
See application file for complete search history.

(56) References Cited

U.S. PATENT DOCUMENTS

| | | |
|---|---|---|
| 721,655 A | 3/1903 | Angle |
| 1,207,566 A * | 12/1916 | Korbitz ................. A61C 7/282 433/12 |
| 3,036,380 A | 5/1962 | Martinek et al. |
| 3,111,758 A | 11/1963 | Winkler, Sr. |
| 3,137,841 A | 6/1964 | Ryder |
| 3,293,747 A * | 12/1966 | Denholtz ................. A61C 7/00 433/21 |
| 3,311,978 A | 4/1967 | Haas et al. |
| 3,314,151 A | 4/1967 | Rubin |
| 3,429,044 A | 2/1969 | Rubin |
| 4,212,637 A | 7/1980 | Dougherty et al. |
| 5,037,296 A * | 8/1991 | Karwoski ................ A61C 7/00 433/22 |
| 5,622,495 A * | 4/1997 | Chikami ................. A61C 7/12 433/22 |
| 5,967,774 A * | 10/1999 | Teramoto ............... A61C 7/282 433/18 |
| 9,066,775 B2 * | 6/2015 | Bukhary .................. A61C 7/22 |
| 9,089,385 B2 * | 7/2015 | Lee ........................ A61C 7/10 |
| 2002/0025501 A1 * | 2/2002 | Clark ...................... A61C 7/00 433/18 |
| 2005/0130094 A1 * | 6/2005 | Graham .................. A61C 7/12 433/20 |

* cited by examiner

*Primary Examiner* — Ralph A Lewis
(74) *Attorney, Agent, or Firm* — Emerson Thomson Bennett; Roger D. Emerson; Nicholas J. Bagnolo

(57) ABSTRACT

Provided are orthodontic devices to orthopedically expand the upper jaw including a pre-formed arch wire adapted to conform to the interior contours of a patient's mouth. The arch includes a rear portion positioned at a level about a patient's rear molars and includes a first end and a second end adapted to slidably engage associated buccal tubes. The arch also includes a front portion positioned at a level above a patient's gingiva and into the patient's vestibule, and a rise portion between the rear portion and front portion that changes the effective level of the arch wire from the rear portion to the front portion. The device also includes a means for attaching the wire to the molar teeth.

20 Claims, 6 Drawing Sheets

METHOD AND APPARATUS FOR SLOW PALATE EXPANSION

TECHNICAL FIELD

The present invention relates to orthodontic devices. More particularly, the present invention is directed at an improved device for orthopedically expanding the upper jaw to gain a better relationship with the lower jaw and to make space for irregular teeth.

BACKGROUND

Orthodontic devices are used to treat irregularities in teeth and jaws. For patients with minor irregularities braces are sufficient to correct these issues. Often however, the use of braces as a lone treatment is not sufficient. In the common case of crowding, a palatal expander is needed to widen the upper and lower jaws to improve the fit between the upper and lower teeth, and to make space for any irregularly crowded teeth.

Palate expansion can be classified into two categories of expansion: slow and rapid expansion. Slow expansion expands the palate at a rate of 0.5 to 1 mm per week as is associated with greater stability and permanency.

A commonly used device for slow palatal expansion is the Kloehn face bow. The face bow and variations are shown in U.S. Pat. Nos. 721,655, 3,036,380, 3,111,758, 3,137,841, 3,311,978, 3,314,151, and 3,429,044. In general, the Kloehn face bow includes an inner bow which attaches inside a patient's mouth to a patient's molar teeth and an outer bow outside of the mouth that is attached to an external strap to be worn around a patient's head or neck.

When expanding, the inner arch wire of the Klohen tips the crowns buccally. The outer bow and pull of the neck straps tip the crowns lingually. Ultimately, one effect cancels the other, resulting in a bodily lateral expansion force. The large, well anchored, tripod roots of the first molars offer more than enough anchorage to cause the mid-palatal suture to grow. This well-established method results in a molar anchorage that is 75-80% efficient. For improved expansion results, it is desirable to increase the molar anchorage efficiently.

U.S. Pat. No. 4,212,637 sought to improve the safety of the device by creating a Kloehn like device with an outer bow that was separable from the inner bow. However, with the outer bow being capable of being removed, it is possible that a user of this device may choose to not to wear the outer bow, decreasing compliance as well as the efficiency of the device. Thus, it is desirable to have a more attractive device that increases compliance and simultaneously maintains proper anchorage efficiency, thus making it an overall more efficient device.

It is also known in the art to provide auxiliary wires 7-10 mm from each end of the arch wire to provide an additional anchoring location of the arch wire and prevent rotation and tipping of the attached molars.

SUMMARY OF THE DISCLOSURE

Disclosed herein are palatal expansion devices without an unattractive outer bow having increased molar anchorage efficiency. The devices and methods disclosed herein support a technique to orthopedically expand the maxillary bone permanently and orthodontically create space for crowded teeth.

In accordance with one aspect of the disclosure an orthodontic device includes an arch wire adapted to be positioned inside a patient's mouth. In some embodiments, the arch wire is a pre-formed wire adapted to conform to the contour of a patient's mouth. The arch wire includes a rear portion, wherein the rear portion is positioned at a level about a patient's rear molars and includes a first end and a second end; wherein the first and second ends are adapted to slidably engage associated buccal tubes. The arch wire also includes a front portion; wherein the front portion is positioned at a level above a patient's gingiva and into the patient's vestibule, and a rise portion, between the rear portion and front portion, wherein the rise portion changes the effective level of the arch wire from the rear portion, positioned about a person's molars, to the front portion, positioned above a patient's gingiva and into the patient's vestibule. The device also includes a means for attaching the wire to a pair of teeth.

In accordance with one aspect of the disclosure, the cross-section of the arch wire is selected from the group including a substantially D-shaped cross section, a substantially H-shaped cross-section, a substantially X-shaped cross-section, a substantially +-shaped cross-section, a substantially rectangular-shaped cross-section, a substantially circular-shaped cross-section, and a substantially oval-shaped cross-section.

In accordance with another aspect of the disclosure, the arch wire further includes an inner facing surface and an outer facing surface, wherein the inner facing surface is a concave surface facing a patient's gingiva and the outer facing surface is a convex surface facing a patient's buccal and labial vestibular tissue.

In accordance with another aspect of the disclosure, the front and rise portions of the arch wire include inner facing surfaces and outer facing surfaces, wherein the inner facing surfaces are substantially concave surfaces facing a patient's gingiva and the outer facing surfaces are convex surfaces facing a patient's buccal and labial vestibular tissue. The rear portions of the device have a cross-section that is the same as the front portion or is different and selected from but not limited to the group including a substantially D-shaped cross section, a substantially H-shaped cross-section, a substantially X-shaped cross-section, a substantially +-shaped cross-section, a substantially rectangular-shaped cross-section, a substantially circular-shaped cross-section, and a substantially oval-shaped cross-section.

In accordance with one aspect of the disclosure, the first end and second ends of the arch wire are beveled to aid insertion of the arch wire ends into associated attachment means/buccal tubes.

In accordance with another aspect of the disclosure, a device includes a first and second ring, wherein the first ring is attached to the arch wire between the rear portion and rise portion of the first end and the second ring is attached to the arch wire between the rear portion and rise portion of the second end, wherein when the first and second ends are slideably engaged in the associated buccal tubes, the rings provide a stop, restricting additional rearward movement, when the first and second rings contact the associated buccal tubes.

In accordance with another aspect of the disclosure, the first and second rings each have an inner facing surface and an outer facing surface, wherein the inner facing surface is a concave surface facing a patient's gingiva and the outer facing surface is a convex surface facing a patient's buccal and labial vestibular tissue, wherein the first ring is attached between the rear portion and rise portion of the first end and the second ring is attached between the rear portion and rise portion of the second end, and wherein when the first and second ends of the rear portion of the arch are slideably engaged in the associated buccal tubes the rings provide a stop when in contact with the associated buccal tubes.

In accordance with another aspect of the disclosure, an orthodontic device further includes at least one washer, wherein the washer has an aperture adapted to slidably engage the arch wire and is placed between the first or second rings and attachment means.

In accordance with another aspect of the disclosure, an orthodontic device further includes an elongated appendage adapted to be secured to the front portion of the arch, wherein the elongated appendage extends into the labial musculature of a patient.

In accordance with another aspect of the disclosure, the elongated appendage is plastic or nylon material. In some embodiments the elongated appendage is bonded or fused to the front portion of the arch wire. In other embodiments the elongated appendage snap fits to the arch wire.

In some embodiments, and in accordance with another aspect of the disclosure, the orthodontic device includes first and second auxiliary wires each having a front end and a rear end; wherein the front ends of the first and second auxiliary wires are attached to the main arch wire between the rear portion and rise portion. The rear ends of the auxiliary wires are adapted to slideably engage a second attachment means.

Also described herein are inventive methods for expanding a patient's palate. A patient's dental arch is measured, a means for anchoring an orthodontic device is attached or banded to selected rear teeth of the patient, an arch adapted to be positioned inside a patient's mouth a pre-formed wire adapted to conform to a the contour of a dental arch of a patient and having a rear portion wherein the rear portion is positioned at a level about a patient's rear molars and includes a first end and a second end; wherein the first and second ends are adapted to slidably engage associated tubes attached to said means for anchoring; a front portion, wherein the front portion is positioned at a level above a patient's gingiva and into the patient's vestibule; a rise portion between the rear portion and front portion wherein the rise portion changes the level from the rear portion positioned about a person's molars to the front portion positioned above a patient's gingiva and into the patient's vestibule.

After several weeks the patient's palate will slowly expand, if more expansion is desired the arch wire can be removed and expanded, meaning that the radius of curvature of the device is increased by bending the rear portions of the device outward. In some cases replacing the arch with a larger arch wire may be preferred.

In accordance with another aspect of the present disclosure the method includes proving an arch wire including a first and second ring, wherein the first ring is attached between the rear portion and rise portion of the first end and the second ring is attached between the rear portion and rise portion of the second end, wherein when the first and second ends are slideably engaged in the associated buccal tubes, the rings provide a stop, restricting additional rearward movement, when the first and second rings contact the associated buccal tubes. In some embodiments the method includes providing washers wherein the washer has an aperture adapted to slidably engage the arch wire and is placed between the first or second rings and attachment means of the tooth.

In accordance with another aspect of the present disclosure the method includes providing an arch wire including an elongated appendage that is attached to the front portion of the arch wire.

DETAILED DESCRIPTION

Figure 1:
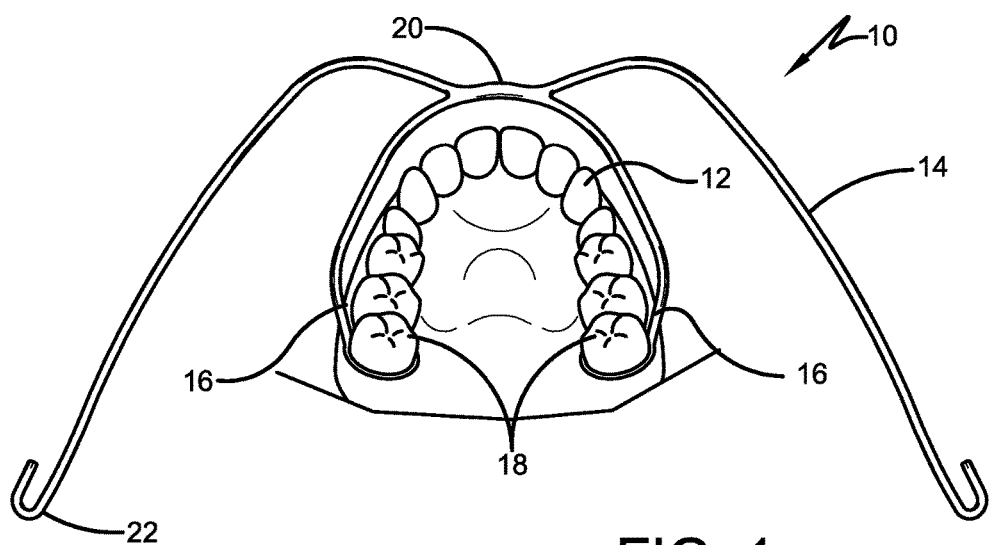
FIG. 1 is a bottom view of a prior art Khoeln device.

The structures shown schematically in the drawings have parts that are examples of the elements recited in the claims. The illustrated structures thus include examples of how a person of ordinary skill in the art can make and use the claimed invention. It is described here to meet the enablement and best mode requirements of the patent statute without imposing limitations that are not recited in the claims. The words used in the claims have their full or ordinary meanings.

The present application contemplates devices and methods, for utilizing an orthodontic slow palatal expansion.

FIG. 1, shows the prior art Kohlen device 10. The device 10 includes an arch wire 12 that is placed inside the patient's mouth and an exterior bow 14 that is outside of the patient's mouth. The inner arch wire 12, is placed in the mouth such that ends of the device are inserted into mounting tubes 16 which are anchored to rear molars 18. The device also includes an exterior bow 14 that is connected to the inner arch wire 12 at point 20. The exterior bow 14 includes ends 22 which are adapted to receive a strap that is worn around the patient's head. When expanding, the inner arch wire 12 of the Koehn 10 tips the crowns of the molars 18 buccally. However with the exterior bow 14 bent up, the pull of a neck strap from an inferior position, tips the crowns of molars 18 lingually. The effects cancel each other out, resulting in a bodily lateral expansion force. The large well anchored tripod roots of the first molars offer more than enough anchorage to cause growth at the mid-palatal suture; thus resulting in the most physiologic and permanent method of apical base expansion.

Figure 2:
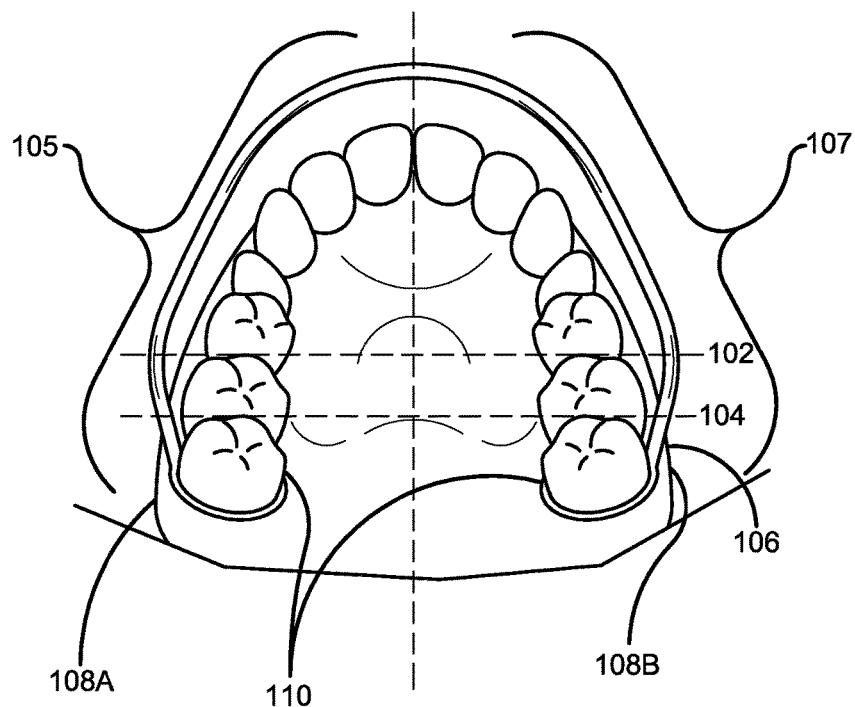
FIG. 2 is bottom view of a device in accordance with the present disclosure.
Figure 3A:
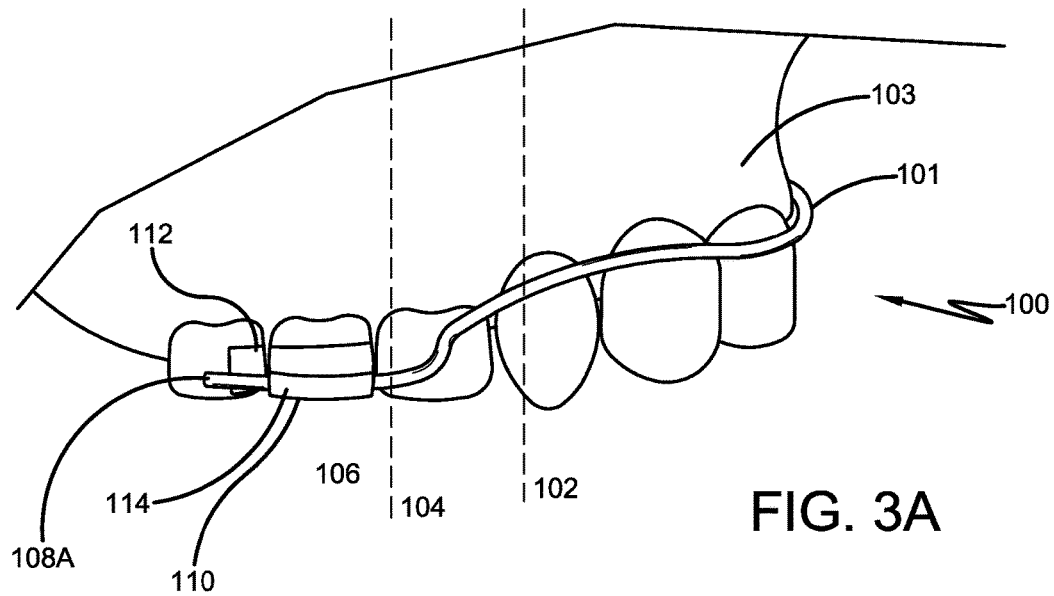
FIG. 3A is a side view of a device in accordance with the present disclosure.

It is an object of this invention to increase the molar anchorage without the bulky and unattractive exterior bow 14. With reference to FIGS. 2 and 3, the palate expander device 100 includes a resilient wire 101 that is generally U-shaped. The wire ends 108A and 108B are adapted extend rearward into a patient's mouth to engage and insert into a set of buccal tubes 114 for attachment. The device applies an outward force, pulling the teeth buccally to expand the palate. The device has a first (right) side 105, a second (left) side 107 and three portions 102, 104, and 106. A front portion 102 sits in the front of a patient's mouth and is positioned above a patient's gingiva 103 and partially extends into the labial musculature of a patient. A rear portion 106 is adapted to be positioned about the rear molars 110 of a patient. The rear portion contains two ends of the arch wire 108A and 108B which slidably engage buccal tubes 114 for attachment to the teeth. A rise portion 104 is located between the rear portion 106 and front portion 102. The rise portion changes the effective level from the rear portion 106, positioned about a patient's molars 110, to the front portion 102, positioned above a patient's gingiva 103. The rise is a step as shown in FIG. 3A or can be a gradual change. However, it is understood that any geometry may be used to change the level from a level about a patient's molars to a slightly higher level above a patient's gingiva 103.

The arch wire 101 should be made of a material that is sufficiently stiff as to eliminate or reduce tooth movement. However, too much force applied could damage a person's mouth. The material should also be compatible in an oral environment, be able to withstand corrosion, and be non-toxic for patients. 18/8 stainless steel is commonly chosen in dental applications for these desirable characteristics. In accordance with one aspect of the disclosure the arch wire ranges in size from 0.040 to 0.060 inches in diameter.

With continued reference to FIG. 3A, buccal tubes 114 are mounted to rear molars. The buccal tubes 114 can be fixed to the molars themselves or to attachment bands 112 which are secured to the rear molars 110. The buccal tubes 114 are adapted to receive a first end 108A and a second end 108B of the rear portion 106 of arch wire 101.

Figure 3B:
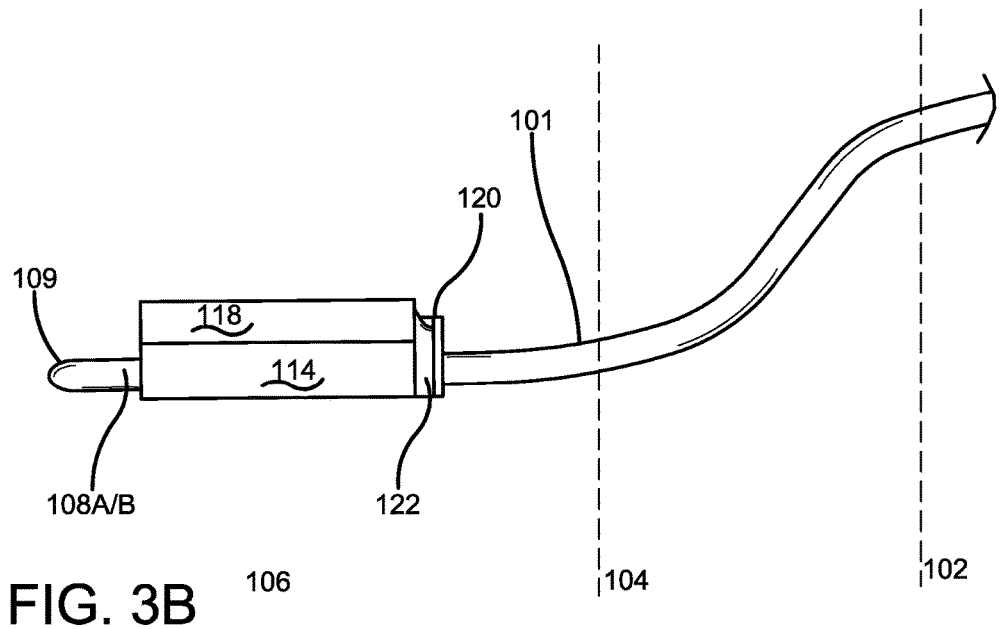
FIG. 3B is an expanded side view of a device in accordance with the present disclosure.

In some embodiments the ends of the wires 108A and 108B are beveled, as shown in FIG. 3B at 109, to aid in insertion of the arch wire 101 into the buccal tube 114.

Figure 3C:
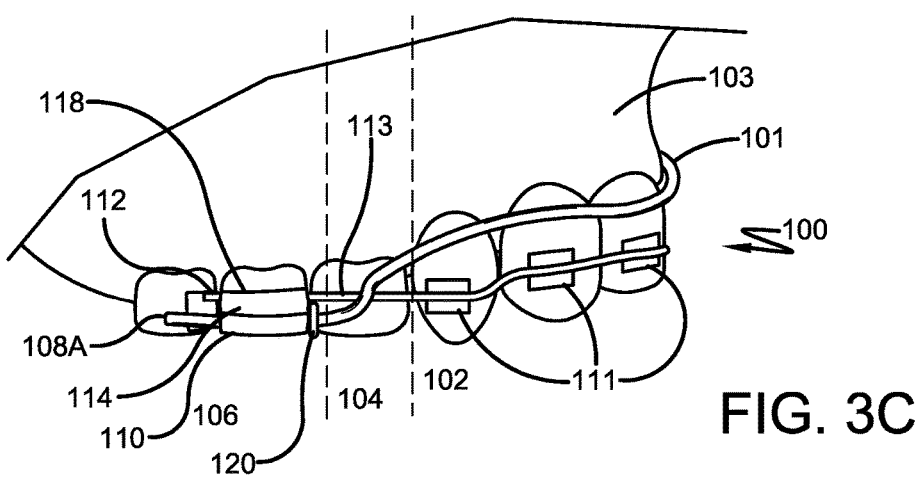
FIG. 3C is an side view of a device in accordance with the present disclosure.

With reference to FIG. 3B and 3C, rings 120 are fixed to the arch wire 101 between the rise portion 104 wire ends 108. The ring 120 diameter is larger than the diameter of the buccal tubes 114 and prevents the device 100 from sliding toward the back of the mouth. The rings 120 are permanently fixed to the arch wire 101 with a solder or adhesive. In some embodiments the rings 120 are removably attached to the arch wire 101. For additional anterior-posterior movement, washers 122 are interposed between the buccal tubes 114 and rings 120. The washers advance the arch device forward and induce a larger separating force in the device which is applied to the rear teeth. Depending on the desired advancement of the device multiple washers are added or removed.

With reference to FIG. 3C, the secondary attachment means/auxiliary buccal tubes 118 are adapted to accept standard 18×25 wire 113 used for braces 111.

Figure 4A:
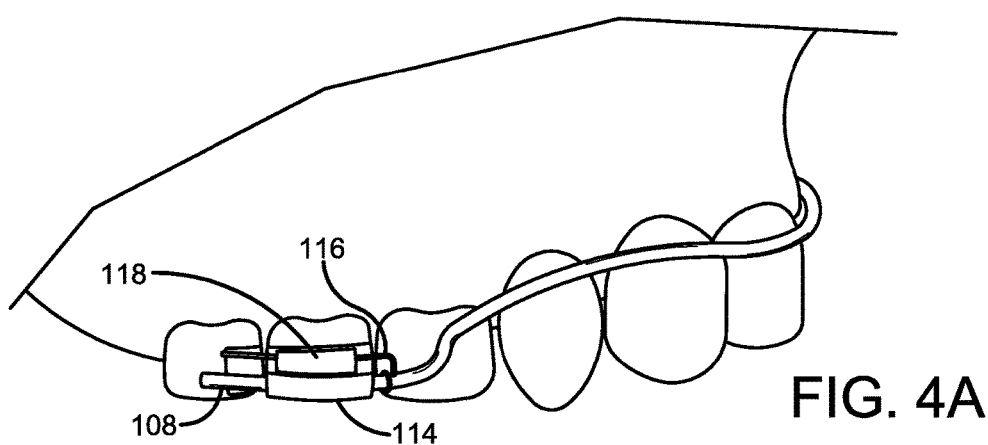
FIG. 4A is a side view of another device in accordance with the present disclosure.
Figure 4B:
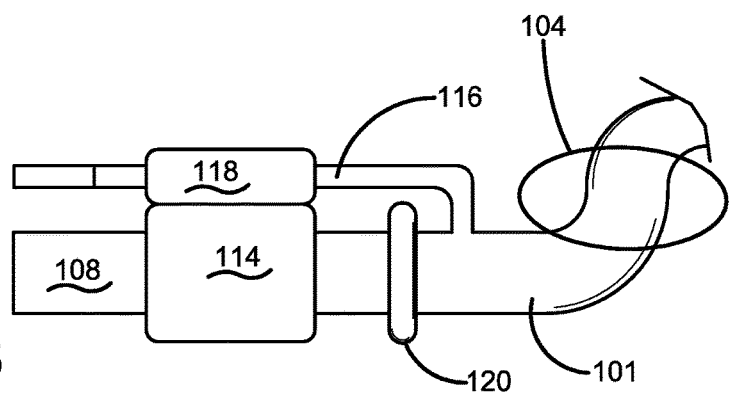
FIG. 4B is an expanded side view of a device in accordance with the present disclosure.

In some cases it may be desirable to provide an additional anchoring point for the arch wire 101. With reference to FIG. 4A-4B, auxiliary wires 116 are attached to the arch wire 101 adding an additional anchoring location of the device to the teeth to prevent rotation. The auxiliary wires 116 are attached approximately 7-12 mm from each end 108A and 108B, of the rear portion 106 and before the rise portion 104 of the arch 100. Auxiliary buccal tubes 118 are additionally fixed to the molars or attachment bands 112 and are adapted to receive the auxiliary wires 116.

In accordance with one aspect of the disclosure the auxiliary wires are round and are the same size as the main arch wire. In accordance with another aspect of the disclosure the round auxiliary wires are a smaller size than the main arch wire and range from 0.010 to 0.050 inches in diameter. According to another aspect of the disclosure, the round auxiliary wires are between 0.010 and 0.020 inches in diameter.

With reference to FIG. 4B, rings 120 are fixed to the arch wire 101 between the attachment point of the auxiliary wires 116 and end portion 108. The ring diameter is larger than the diameter of the buccal tubes 114 and prevents the device from sliding toward the back of the mouth. The rings 120 are usually permanently fixed to the arch wire 101 with a solder or adhesive. In some embodiments the rings 120 are removably attached the arch wire 101.

Figure 4C:
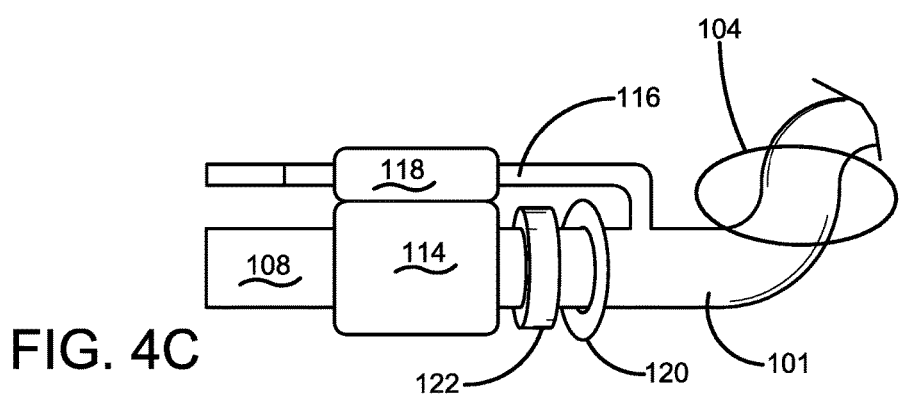
FIG. 4C is an expanded side view of a device in accordance with the present disclosure.

In some embodiments, as shown in FIG. 4C, for additional anterior-posterior movement, washers 122 are interposed between the buccal tubes 114 and rings 120. The washers advance the arch device forward and induce a larger separating force in the device which is applied to the rear teeth. This separating force results in the posterior movement of the rear teeth, thereby increasing the space between the teeth in the anterior-posterior plane.

Figure 5A:
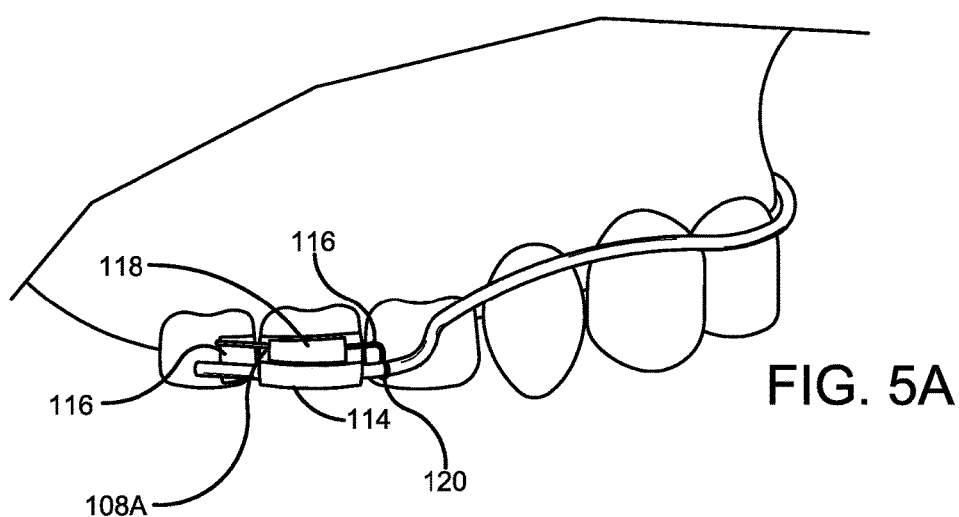
FIG. 5A is a side view of another device in accordance with the present disclosure.
Figure 5B:
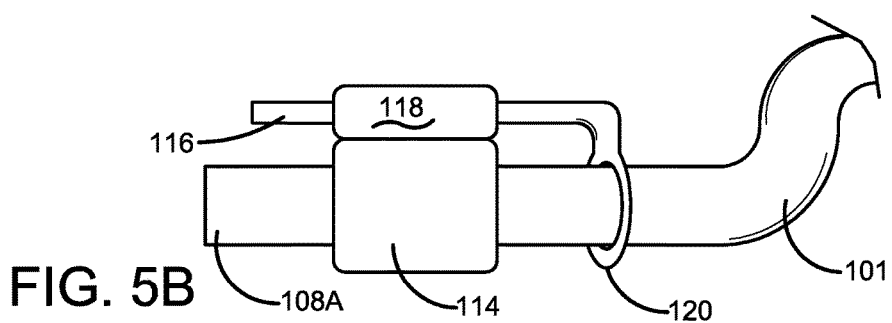
FIG. 5B is a close up illustration of the device of FIG. 5A.
Figure 5C:
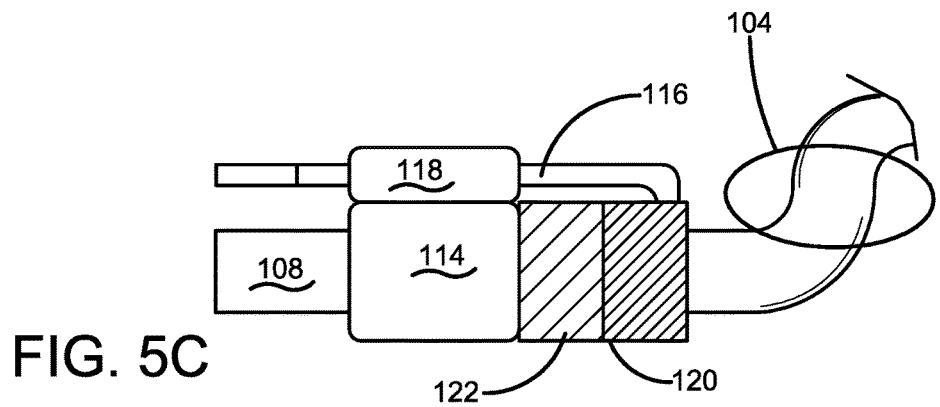
FIG. 5C is a close up illustration of the palate expander auxiliary wire.

During development and as illustrated in FIGS. 5A-5C, rings 120 were fixed to the rear portion of the device, separating the front 102 and rise portions 104 of the arch from the rear portion 108 for attachment. The ring diameter was larger than the diameter of the buccal tubes 114 and prevented the device 100 from sliding toward the back of the mouth. In these embodiments, the rings 120 also provided a location for the attachment of auxiliary wires 116. For additional anterior-posterior movement, as illustrated in FIG. 5C, washers 122 were interposed between the buccal tubes 114 and rings 120. The washers 122 advanced the arch forward and induced a larger separating force in the device which is applied to the rear teeth.

Figure 6:
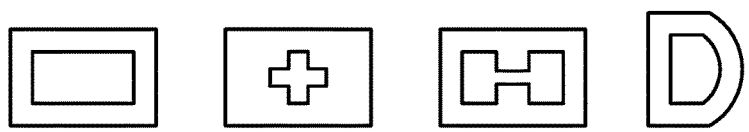
FIG. 6 illustrates cross-sections of arch wires and attachment means in accordance with the present disclosure.

The cross-section of the arch wire 101 is chosen for its ability to resist rotation and for its comfort level. The cross-sections are selected from but are not limited to, the cross-sections shown in FIG. 6. While FIG. 6 illustrates the openings and shape of the interior of the corresponding buccal tubes, it is understood that an arch wire 101 to be inserted in the buccal tube 114 will be of a matched shape. The shapes shown in FIG. 6 show a substantially D-shaped cross section, a substantially H-shaped cross-section, a substantially X-shaped cross-section, a substantially +-shaped cross-section, a substantially rectangular cross-section, a substantially circular cross-section, and a substantially oval cross-section. The buccal tubes 114 are adapted to engage the chosen arch wire cross-section shape.

Figure 7:
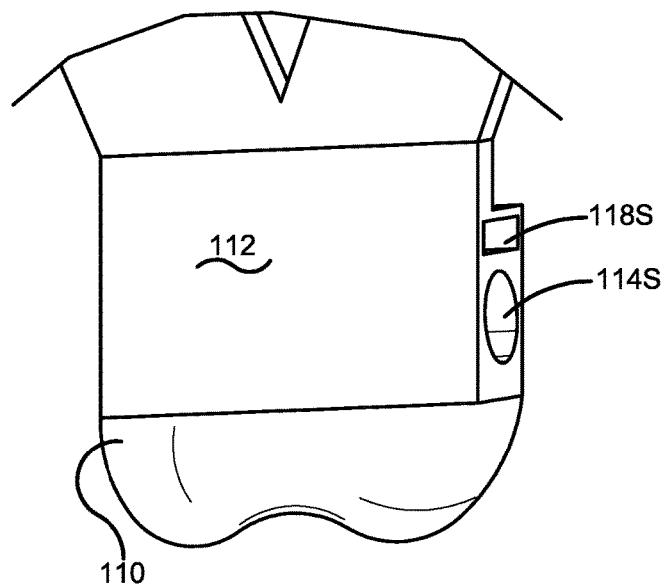
FIG. 7 illustrates an attachment means in accordance with the present disclosure.
Figure 8:
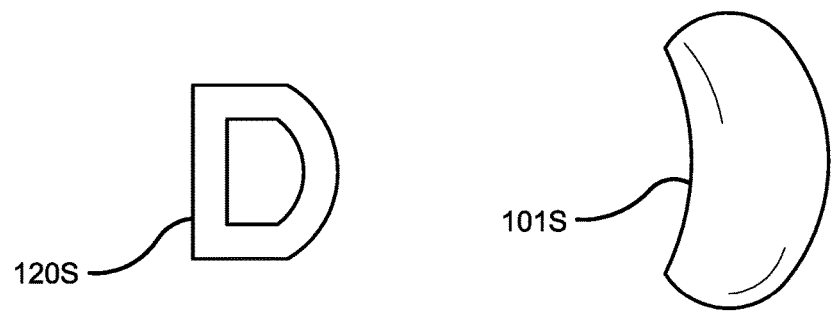
FIG. 8 illustrates cross-sections of rings and arch wires in accordance with the present disclosure.

Referring to FIG. 7, according to some embodiments, the attachment means can include an attachment band 112 that is secured around the circumference of the molar 110. The attachment means includes buccal tubes 114S designed and shaped to accommodate the insertion of a correspondingly shaped arch wire 101S, the cross-section as shown in FIG. 8. The attachment means also includes additional buccal tubes 118S that are designed and shaped to accommodate the insertion of correspondingly shaped auxiliary wires 116 or braces wire 113.

In accordance with one aspect of the disclosure and as shown in FIG. 8, the rings 120S can be shaped to provide comfort to the patient. The inner facing surface can be either flat or concave to match to a patient's gingiva while the outer facing surface can be a convex surface facing the buccal and labial vestibular tissue.

In accordance with another aspect of the disclosure, the front and rise portions, 102 and 104 respectively, of the arch wire 101S include inner facing surfaces toward to gum, and outer facing surfaces toward the lip and cheek, as shown in FIG. 8, wherein the inner facing surface can be either flat or concave to match to a patient's gingiva while the outer facing surface can be a convex surface facing the buccal and labial vestibular tissue. The rear portions 106 of the device include cross-sections that are the same as the front portion 102 or are different and selected from, but not limited to the group including a substantially D-shaped cross section, a substantially H-shaped cross-section, a substantially X-shaped cross-section, a substantially +-shaped cross-section, a substantially rectangular-shaped cross-section, a substantially circular-shaped cross-section, and a substantially oval-shaped cross-section.

Figure 9:
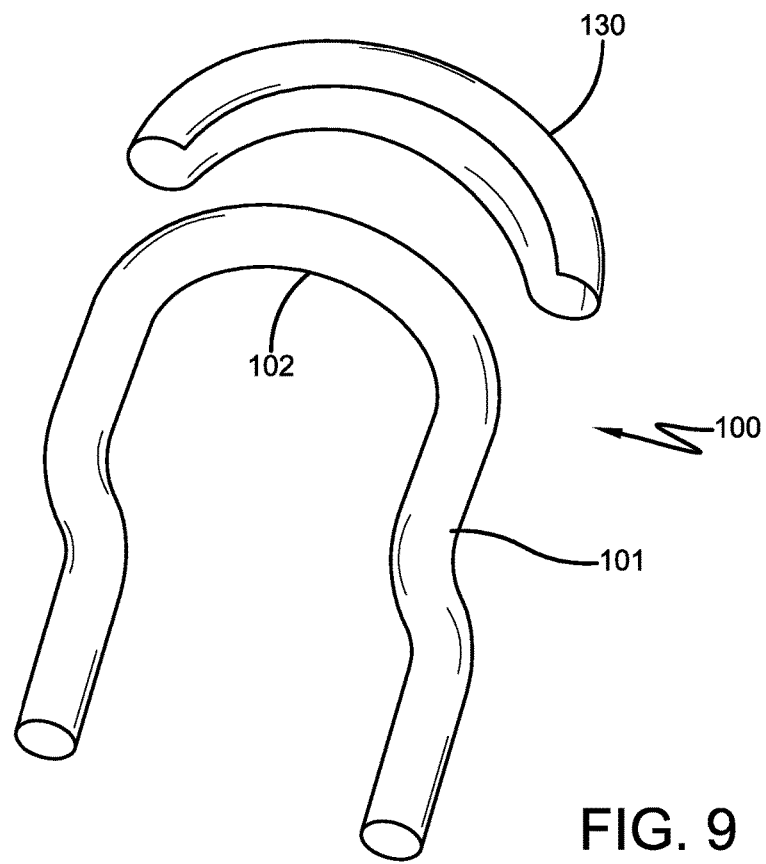
FIG. 9 illustrates another embodiment of an orthodontic device in accordance with the present disclosure.

Referring now to FIG. 9, in accordance with another aspect of the disclosure, the orthodontic device 100 further includes an elongated appendage 130 adapted to engage the front portion 102 of the arch wire 101, wherein the elongated appendage 130 extends into and pushes against the labial musculature of a patient. Presence of the arch wire pushing into and against the labial musculature activates the stretch reflex property of the muscle. The addition of the appendage increases the surface area of the arch wire and increases the muscle response. The more the muscle is stretched the more it pushes back. This effect drives the molars posteriorly as effectively as cervical pull from the outer bow of a face bow Kloehn device. When coupled with the advancement of the arch wire 101 through use of washers 122, the additional surface area and resulting musculature push back results in the posterior movement of the rear teeth, thereby increasing the space between the teeth in the anterior-posterior plane.

In accordance with one aspect of the disclosure, the elongated appendage 130 is made of plastic. In accordance with another aspect of the disclosure a material such as nylon can be molded, fused, or bonded to the wire to create the appendage.

In accordance with another aspect of the disclosure the elongated appendage 130 can be designed such that it can snap fit to the arch wire 101.

A method or process of treatment for expanding a patient's palate can progress as follows: First the arch size of the patient is measured. A wire or string spanned from molar to molar would measure the arch length. The measured arch length is then adjusted to add an additional length corresponding to the total size needed for the device's arch wire 101. In most applications, the increase in length should fall into a range of 3-5 mm, with extremes of 1-10 mm. The wire is bent and the ends 108A and 108B are slideably engaged in buccal tubes attached to rear molars. Over time, while worn, the orthodontic device 100 can expand a patient's palate by a measure ranging from 8-12 mm. The patient would then be seen again by the Orthodontist, usually between every eight to ten weeks. If more adjustment/expansion is required, the radius of curvature of the arch wire is simply expanded by between 5-8 mm and reinserted into the tubes. The process repeats until the desired total expansion is reached. For some treatments it is desirable to replace the original arch wire with a new longer arch wire.

EXAMPLE 1

An early attempt to create a 100% efficient orthodontic device for the most abundant orthodontic case, Class I crowding, was to use a 0.045" diameter expanded 18/8 steel arch wire. The ends of the main wire fit into 0.045" buccal tubes that were anchored to a patient's rear molars. Here the tubes were attached to a metal anchoring band that wrapped around the circumference of a molar. Auxiliary wires were soldered to the main wire about 9-10 mm from each end of the wire. Auxiliary tubes were mounted to each anchoring band, above each 0.045" buccal tube. The presence of the auxiliary wires and auxiliary tubes provided an additional location for molar anchoring. It was estimated that this device was 80-85% efficient.

EXAMPLE 2

To increase efficiency, simplify, and gain up to 100 percent performance that was lacking in the previous example, the 0.045" diameter steel wires were pre-formed to five different parabolic shapes. Each pre-formed arch wire included a small ring attached to the wire about 7 to 10 mm from each end. The portion of the arch wire from the rings to the ends define the attachment portion of the arch wire while the portion of the arch wire in between the two rings define the working area of the arch. The attachment portion of the arch wire was beveled as it allowed easy slidable insertion into modified buccal tubes that were modified to have an internal anatomy identical to the form of the arch wire. The rings attached to the arch wire prevented over insertion of the device.

Presence of the arch pushing into the labial musculature activated the stretch reflex property of the muscle. The device was advanced further into the labial musculature by adding washers around the wires between the fixed wire rings and mounting tubes. The further the advancement, the more the muscle was stretched the more it pushed back. This effect drove the molars posteriorly as effectively as cervical pull from the outer bow of a face bow Kloehn device. Thus, this device accomplishes the task of the Kloehn device completely inter-orally and the external bow of the Kloehn device is no longer needed.

Having thus described the invention, it is now claimed:

I claim:

1. An orthodontic device comprising:
   an arch adapted to be positioned inside a patient's mouth, wherein the arch is adapted to cross between an anterior-posterior plane within the patient's mouth, the arch comprising:
      an arch wire adapted to conform to the contour of a patient's mouth and having a rear portion, a front portion and a rise portion,
      wherein the arch wire comprises an inner facing surface and an outer facing surface, wherein the inner facing surface of the arch wire is adapted to face a patient's gingiva and the outer facing surface of the arch wire is adapted to face a patient's buccal and labial vestibular tissue;
      wherein the rise portion is located between the rear and front portion;
      wherein the rear portion is adapted to be positioned level with a patient's rear molars or rear teeth and includes a first end and a second end to engage first and second buccal tubes that are adapted to be attached to the teeth, wherein the first end and second end are beveled;

wherein the front portion is adapted to be positioned at a level above a patient's gingiva and into the patient's vestibule;

wherein the rise portion changes the level from the rear portion to the front portion; and wherein the buccal tubes are adapted to be either fixed to the teeth or to the attachment bands which are secured to the teeth;

a first ring and a second ring, wherein the first ring is attached to the arch wire between the rear portion and the rise portion of the first end of the arch wire, wherein the first ring is positioned adjacent to the first buccal tube and wherein the first ring is permanently fixed to the arch wire, wherein the second ring is attached to the arch wire between the rear portion and the rise portion of said second end of the arch wire, wherein the second ring is positioned adjacent to the second buccal tube, and wherein the second ring is permanently fixed to the arch wire, wherein the first ring and the second ring have a diameter that is larger than that of the first and second buccal tubes so that when the first ring and the second ring are engaged with the buccal tubes, the first ring and the second ring operatively prevent the orthodontic device from sliding in a rearward direction within the patient's mouth, wherein the orthodontic device orthopedically expands the maxillary bone permanently and orthodontically to create a space for crowded teeth.

2. The orthodontic device of claim 1 wherein the cross-section of the arch wire is selected from the group consisting of a substantially D-shaped cross section, a substantially H shaped cross-section, a substantially X-shaped cross-section, a substantially +-shaped cross section, and a substantially oval-shaped cross-section.

3. The orthodontic device of claim 1 wherein the inner facing surface of the arch wire is a concave surface facing a patients gingiva and the outer facing surface of the arch wire is a convex surface facing a patient's buccal and labial vestibular tissue.

4. The orthodontic device of claim 1 wherein the rear portion comprises a cross-section of the arch wire selected from the group consisting of a substantially D-shaped cross section, a substantially H shaped cross-section, a substantially X-shaped cross-section, and substantially +-shaped cross-section, a substantially rectangular shaped cross-section, a substantially circular shaped cross-section, and a substantially oval-shaped cross-section and; the front portion of the arch wire further comprises an inner facing surface and an outer facing surface, wherein the inner facing surface is a concave surface facing a patients gingiva and the outer facing surface is a convex surface facing a patient's buccal and labial vestibular tissue.

5. The orthodontic device of claim 1 further comprising: first and second auxiliary wires each having a front auxiliary wire end and a rear auxiliary wire end;

wherein the front auxiliary wire ends of the first and second auxiliary wires are attached to the arch wire between said rear portion and rise portion, and wherein the rear auxiliary wire ends are adapted to engage a second attachment means.

6. The orthodontic device of claim 1, wherein the first and second rings each comprise an inner facing surface and an outer facing surface;

wherein the inner facing surface is a concave surface facing a patient's gingiva and the outer facing surface is a convex surface facing a patient's buccal and labial vestibular tissue.

7. The orthodontic device of claim 1, further comprising at least one washer;

wherein the at least one washer comprises an aperture adapted to slidably engage the arch wire, wherein the at least one washer is placed between either the first ring or the second ring and the buccal tube to advance the arch of the device forward and induce a larger separating force in the orthodontic device which is applied to the rear teeth and wherein the separating force results in posterior movement of the rear teeth, thereby increasing the space between the teeth in the anterior-posterior plane.

8. The orthodontic device of claim 1 further comprising: an elongated appendage adapted to be secured to the front portion of the arch wire, wherein the elongated appendage extends into the labial musculature of a patient.

9. The orthodontic device of claim 8 wherein the elongated appendage is a plastic material.

10. The orthodontic device of claim 9, wherein the elongated appendage is molded or fused to the front portion of the arch wire.

11. The orthodontic device of claim 9, wherein the elongated appendage snap fits to the front portion of the arch wire.

12. The orthodontic device of claim 1, wherein the device further comprises a set of secondary buccal tubes wherein the secondary buccal tubes are adapted to accept a set of auxiliary wires attached to the arch wire, wherein the secondary buccal tubes and auxiliary wires provide an additional location for anchoring the orthodontic device to the teeth to prevent rotation and wherein the first ring and the second ring are fixed to the arch wire between the auxiliary wire attachment point and the end portion.

13. The orthodontic device of claim 12, wherein the device further comprises at least one washer interposed between the buccal tube and the ring at the first end and/or the second end of the arch wire to advance the arch device forward and induce a larger separating force in the orthodontic device which is applied to the rear teeth.

14. The orthodontic device of claim 12, wherein the auxiliary wires are attached to the first ring and the second ring.

15. The orthodontic device of claim 14, wherein at least one washer is interposed between the buccal tube and the ring of the first end and/or the second end of the arch wire to advance the arch device forward and induce a larger separating force in the orthodontic device which is applied to the rear teeth.

16. The orthodontic device of claim 12, wherein the auxiliary wires are braces.

17. A method of expanding a patient's palate comprising:
measuring the dental arch size of a patient;
providing the orthodontic device of claim 1;
anchoring the orthodontic device to a patient's selected rear teeth;
adding at least one washer between the first ring or the second ring and the buccal tube advancing the wire arch into a patients labial musculature; and
attaching an elongated appendage adapted to be secured to the front portion, wherein the elongated appendage extends into the labial musculature of a patient.

18. A method for expansion of the mid-palatal and inter-maxilliary suture of a patient, the patient having a mouth having gingiva, a vestibule, having teeth in bone and defining a mouth contour, the method comprising:
  operationally engaging an apparatus between a first tooth and a second tooth of the patient, the first tooth and the second tooth being on opposite sides of the mid-palatal and inter-maxilliary suture of the patient, the apparatus having:
    an elongated arch,
      crossing between an anterior-posterior plane within the mouth,
      having a rear portion, the rear portion having
        a first beveled end of the elongated arch, and
        a second beveled end of the elongated arch;
      having a front portion positioned at a level above the gingiva of the patient and into the vestibule of the patient,
      having a rise portion between the rear portion and the front portion, the rise portion providing a vertical offset between the rear portion and the front portion,
      having an arch wire adapted to conform to the mouth contour, the arch wire having:
        an inner facing surface, and
        an outer facing surface,
          wherein the inner facing surface of the arch wire faces gingiva of the mouth and the outer facing surface of the arch wire faces buccal and labial vestibular tissue of the mouth;
  engaging a first buccal tube having a first diameter to the first tooth;
  engaging a second buccal tube having a second diameter to the second tooth;
  engaging the first end of the elongated arch with the first tooth using the first buccal tube;
  engaging the second end of the elongated arch with the second tooth using the second buccal tube;
  engaging a first ring and a second ring,
    wherein the first ring is attached to the arch wire between the rear portion and the rise portion of the first end of the arch wire, wherein the first ring is positioned adjacent to the buccal tube towards the rise portion and wherein the first ring is permanently fixed to the arch wire,
    wherein the second ring is attached to the arch wire between the rear portion and the rise portion of said second end of the arch wire, wherein the second ring is positioned adjacent to the buccal tube towards the rise portion, and wherein the second ring is permanently fixed to the arch wire,
    wherein the first ring has a diameter that is larger than that of the diameter of the first buccal tube so that when the first ring is engaged with the first buccal tube, the first ring operatively prevents the orthodontic device from sliding in a rearward direction within the patient's mouth,
    wherein the second ring has a diameter that is larger than that of the diameter of the second buccal tube so that when the second ring is engaged with the second buccal tube, the second ring operatively prevents the orthodontic device from sliding in a rearward direction within the patient's mouth,
  applying an orthopedic force to each of the first tooth and the second tooth of sufficient magnitude that the resulting effect is to make each tooth immovable within the bone; and using the orthopedic force to apply tension to the mid-palatal and inter-maxilliary suture of a patient for sufficient duration to cause permanent expansion growth of the mid-palatal and inter-maxilliary suture.

19. The method of claim 18 wherein the magnitude of orthopedic force applied to each of the first tooth and the second tooth,
  is sufficient to interfere with the blood supply surrounding each of the first tooth and the second tooth; and
  is at least 16 ounces.

20. The method of claim 19 wherein the first tooth and the second tooth are prevented from being torqued out of their initial orientation by using a non-round or forked wire to provide a restorative torsion and thereby prevent a net torque on either tooth.

* * * * *